US005759410A

United States Patent [19]
Christ, Jr. et al.

[11] Patent Number: 5,759,410
[45] Date of Patent: Jun. 2, 1998

[54] PROCESS FOR RECOVERING MERCAPTO-S-TRIAZINES FROM SILVER PRECIPITATE

[75] Inventors: Charles S. Christ, Jr., Fairport; Albert R. Szembrot, Penfield; Robert Ciamarra, Tuckahoe, all of N.Y.

[73] Assignee: Eastman Kodak Company, Rochester, N.Y.

[21] Appl. No.: 812,366

[22] Filed: Mar. 5, 1997

[51] Int. Cl.[6] ................................. C02F 1/70; C02F 1/62
[52] U.S. Cl. ..................... 210/711; 210/719; 210/729; 210/912; 75/711; 75/713; 75/721; 75/722; 75/741
[58] Field of Search ............................. 210/711, 729, 210/912, 719; 75/711, 713, 721, 741, 722

[56] References Cited

U.S. PATENT DOCUMENTS

| 5,288,728 | 2/1994 | Spears et al. | 210/729 |
| 5,496,474 | 3/1996 | Christ, Jr. et al. | 210/725 |

*Primary Examiner*—Neil McCarthy
*Attorney, Agent, or Firm*—John R. Everett

[57] ABSTRACT

There is provided a process for converting a silver-mercapto-s-triazine precipitate to a solid containing silver and a solution containing mercapto-s-triazine by contacting the silver-mercapto-s-triazine precipitate with one or more reducing agents. In preferred embodiments, at least one of the reducing agents has a redox potential more negative than about −0.9 V vs. Normal Hydrogen Electrode, NHE.

19 Claims, No Drawings

_(5,759,410)_

PROCESS FOR RECOVERING MERCAPTO-S-TRIAZINES FROM SILVER PRECIPITATE

FIELD OF INVENTION

This invention relates to a process for recovering silver from solutions, such as seasoned photoprocessing solutions.

BACKGROUND OF INVENTION

During the processing of silver halide photographic products, silver is removed from the photographic film and paper by contact with a fixing solution or bleach fixing solution. The silver is generally solubilized by reaction with thiosulfate ion. Such a process results in a solution rich in soluble silver.

Two main reasons exist for the recovery of silver in fixing and bleach fixing solutions. First, there exists a regulatory compliance issue. Second, the silver in the solution has monetary value. Another reason for recovering silver, is to reuse a limited resource. In many cases the recovered silver is used again in manufacturing photographic products. Thus, silver recovery is one step in a recycling process.

There are many techniques for recovering silver from photographic solutions: electrolytic silver recovery, metallic replacement, ion exchange, chemical reduction, and precipitation. Electrolytic silver recovery is one of the most popular methods for the recovery of silver, but is not generally sufficient for those photoprocessors operating in the regulatory compliance mode. Electrolytic techniques do not usually remove silver from photographic solutions to concentrations lower than about 100 ppm. Often a tailing or secondary silver recovery method such as metallic replacement is also necessary. Ion exchange methods are more suited to dilute silver bearing streams such as wash water.

Recently, precipitation processes for recovering silver using chemical precipitants known as mercapto-s-triazines have been disclosed in U.S. Pat. Nos. 5,288,728, 5,437,792, 5,476,593 and 5,496,474. Trimercapto-s-triazine (TMT) is a preferred precipitant and is often used in salt form. The precipitation method is a continuous process that replaces both primary and secondary silver recovery with a single process utilizing silver precipitation, flocculation and filtration. The process is simple to use, neat, and consistently allows the photoprocessor to remain in regulatory compliance with respect to silver levels in the photographic effluent. The silver-mercapto-s-triazine precipitate is easily refined and considered to be a good feed for certain refining operations.

The mercapto-s-triazine precipitation techniques are costly due to the cost of the mercapto-s-triazines such as TMT which limits their use. A possible scenario for lowering the cost of mercapto-s-triazines would be through their recovery from the silver-mercapto-s-triazine precipitate. Presently, the refining process for the silver-mercapto-triazine precipitant begins with heating the precipitate and destruction and loss of the mercapto-s-triazine portion of the solid. It is desirable to provide a refining process which allows the mercapto-s-triazine portions to be recycled.

Other techniques used to recover silver from photoprocessing solutions involve contacting a reducing agent with the silver bearing solution. In the vast majority of cases, the reaction is homogeneous, i.e., the reaction occurs between a dissolved silver species and a dissolved reducing agent. These processes have not found wide use in the photoprocessing trade because the reducing agents used are often strong enough to reduce the water solvent and produce hydrogen gas. Safety concerns in the use and handling of such reducing agents makes widespread use in on-site treatment unpopular. An example of a heterogeneous reduction reaction has been disclosed in U.S. Pat. No. 5,372,631, but involves only the reduction of Ag without any precipitating agent recycling step.

SUMMARY OF THE INVENTION

It is an object of the present invention to reduce the cost of silver recovery by mercapto-s-triazine precipitation techniques.

It is another object of the present invention to provide a process for refining silver from a silver-mercapto-s-triazine precipitate, wherein the mercapto-s-triazine within the precipitate is recovered.

It is a further object of the present invention to provide a process for refining silver from a silver-mercapto-s-triazine precipitate wherein at least a portion of the mercapto-s-triazine within the precipitate is recyclable.

Additional objects will become apparent from the detailed disclosure and claims which follow.

The above objects are achieved through the processes of the present invention wherein the silver-mercapto-s-triazine precipitate is reduced to produce a relatively high purity silver metal precipitate and a solution of mercapto-s-triazine. The high purity silver solid obtained is easily refined as compared to most other recycled silver sources, and the mercapto-s-triazine solution can be reused, after a reconstitution process, to precipitate silver from solutions such as photographic solutions.

The reducing agent is used for two purposes. First, the reducing agent is used to reduce silver from the $Ag^{+1}$ state to the Ag metal state. Second, the reducing agent allows the resolubilization of the mercapto-s-triazine precipitating agent so that it can be reused as a metal recovery agent. The overall process can be viewed as a two-product recycling system, providing a more pure form of silver requiring less energy for further purification and a solution that can easily be converted to a new precipitating solution. Recovery of silver from solution can be performed on-site, while recycling of the mercapto-s-triazine can be performed in a central facility if desired.

DESCRIPTION OF THE PREFERRED EMBODIMENTS OF THE INVENTION

The silver mercapto-s-triazine precipitates employed in the process of this invention are derived from silver recovery processes such as those disclosed in U.S. Pat. Nos. 5,437,792, 5,288,728, 5,476,593 and 5,496,474. These are derived from soluble silver ions and mercapto-s-triazine of the formula I

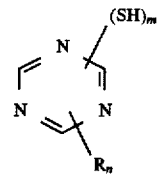

wherein:

R is hydrogen, —$NH_4$, —OH, alkyl having 1 to 8 carbon atoms, alkoxy having 1 to 8 carbon atoms, phenyl, cyclohexyl, oxazinyl, phenoxy, —$NR'_2$ or SR"; wherein R' is hydrogen, alkyl having 1 to 8 carbon atoms, phenyl, cyclohexyl, naphthyl or benzyl; and wherein R" is allyl having 1 to 8 carbon atoms, phenyl, cyclohexyl, naphthyl or benzyl; m is an integer from 1 to 3; and n is 0 or an integer from 1 to 2.

Four factors influence the effectiveness of the process of this invention: reaction temperature, amount of reducing agent, concentration of reducing agent, and power of reducing agent, which can be related to the pH of the reaction slurry. The temperature affects the rate at which the reaction occurs. While the invention may be practiced at reaction temperatures of 15° C. to 100° C., a more effective range is between 30° C. and 75° C., and the best range for the invention is between 45° C. and 65° C. Temperatures below the optimum range require longer times for the reaction to occur and temperatures above the optimum range may lead to decomposition of the mercapto-s-triazine solubilized during the reaction.

At least one molar equivalent of the appropriate reducing agent per mole of Ag is necessary to achieve conversion of the silver-mercapto-s-triazine precipitate to silver metal and solubilized silver-mercapto-s-triazine, according to the generic reaction shown below for trimercapto-s-triazine (I).

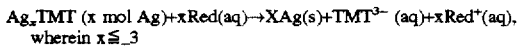
$Ag_xTMT$ (x mol Ag)+xRed(aq)→XAg(s)+$TMT^{3-}$ (aq)+x$Red^+$(aq), wherein x≦3

In the most simple form, the reaction can be described as a one electron reduction of $Ag^+$ to Ag metal.

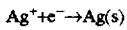
$Ag^+ + e^- \rightarrow Ag(s)$

Where $Ag^+$ is supplied in the form of the Ag-TMT precipitate and the electron is supplied by a suitable reducing agent.

The only complicating factor is that the $Ag^+$ is incorporated in an insoluble precipitate with TMT or other mercapto-s-triazine. The theoretical composition of precipitates is $Ag_xTMT$ (x=3), but in reality the typical composition of the precipitate will have a value of x somewhat less than 3. Therefore, in order to establish the minimum amount of reducing agent necessary to achieve the desired outcome of the invention it is helpful to characterize the precipitate in terms of the total Ag content. Since, a silver-TMT precipitate will never have a value of x greater than 3, calculation of the amount of reducing agent based on the assumption that the precipitate is $Ag_3TMT$ will always provide reducing agent in excess of the minimum theoretical amount necessary for the reaction. A more accurate assessment of the silver content can be obtained using AA (Atomic Absorption) or ICPAES (Inductively Coupled Plasma Atomic Emission Spectroscopy).

Theoretically, only one molar equivalent of the appropriate reducing agent per mole of Ag is necessary to achieve conversion of the silver-mercapto-s-triazine precipitate to silver metal and solubilized mercapto-s-triazine. In practice, the amount of reducing agent necessary to achieve the desired reaction in a reasonable time (less than 1 month) is in excess of the theoretical amount. The reason for the excess is more related to the concentration of the reducing agent than a particular limitation or requirement for the invention.

The concentration of the reducing agent has a strong effect on the rate of the inventive reaction. In the case of $NaBH_4$, concentrations of less than 0.1M give sluggish rates for the conversion of silver-mercapto-s-triazine precipitate to silver metal and solubilized mercapto-s-triazine. Concentrations above about 0.6M give significantly better rates in conjunction with temperatures above about 50° C. The best results can be expected at temperatures of about 55° C. to 60° C. and $NaBH_4$ concentrations above about 0.75M. For $Na_2S_2O_4$, concentrations above 0.1M give satisfactory results, but concentrations greater than 0.3M are preferred and the best concentrations are above 0.4M. Similar concentrations are expected to be preferred for $Na_2SO_3$, where the most preferred concentrations are above 0.4M. In general, reasonably effective concentrations of reducing agent are above about 0.05M, with preferred concentration above 0.3M and the best concentrations above 0.4M with the upper limit as the solubility of the reducing agent.

To be effective in the process of the present invention, the power of the reducing agent must be such that it is more negative than about −0.9 V vs. the Normal Hydrogen Electrode (NHE). The reaction may be conducted at about pH 5 and above. The lower limitation of the pH is related to the precipitation of the mercapto-s-triazines in their fully protonated form, which begins to occur at pH's below about 6. In addition, certain reducing agents with pH-independent reduction potentials will react with water to produce hydrogen. With such reductants, pH's above about 11 are preferred since the thermodynamic driving force for reduction of water is negligible. Maintaning the pH above about 12 is best. For reductants with pH dependent reduction potentials, the pH must be maintained at a value more negative than about −0.9 V vs NHE. Examples are shown below:

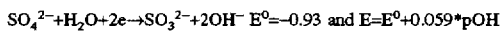
$SO_4^{2-} + H_2O + 2e^- \rightarrow SO_3^{2-} + 2OH^-$  $E^0 = -0.93$ and $E = E^0 + 0.059 \cdot pOH$ So at a pH of 11 (pOH=3), the reducing power of $SO_3^{2-}$ is reduced to −0.753 V vs NHE. Therefore, at a pH of 11, $SO_3^{2-}$ is not a good reducing agent for the inventive reaction, whereas at a pH of 14, $SO_3^{2-}$ is an acceptable reducing agent.

In contrast,

$2\ SO_3^{2-} + 2\ H_2O + 2e^- \rightarrow S_2O_4^{2-} + 2OH^-$  $E^0 = 1.12$ V So at a pH of 11 (pOH=3), the reducing power of $S_2O_4^{2-}$ is reduced to −0.943 V vs NHE but is still sufficiently powerful to carry out the inventive reaction.

Operating at lower pH's will have the general effect of lowering the reducing power of the reductant and will decrease the rate of the reaction with the silver-mercapto-s-triazine precipitant. In addition, for those reductants that have sufficient reducing power to reduce the water solvent, lower pH's will increase the rate at which the reduction of water occurs. As a result the reductant will be consumed in an undesired side reaction, negatively impacting the reaction rate.

The pH can have a significant effect on the choice of reductant. The reaction may be carried out under a variety of pH conditions from about pH 6 to more than pH 14. The lower limit is given by the pH at which the mercapto-s-triazine product precipitates from the solution (pH 6). The upper limit may be above 14. Acceptable pH ranges are above 6 but preferred pH's are above about 12 with the best pH being about 14 and with the most important factor being the reduction potential of the reductant, which must be more negative than about −0.9 V vs NHE.

Regeneration of the TMT Precipitating Solution

After the reaction between the reducing agent and the silver-mercapto-s-triazine precipitate is complete, and the silver solid is separated from the mercapto-s-triazine containing solution, recycling of the mercapto-s-triazine solution can be accomplished by adjusting the level of mercapto-s-triazine, and the pH of the solution. One of the commonly used forms of the mercapto-s-triazine solution is TMT 15 (which is an aqueous solution containing about 15% $Na_3TMT$.) As an example, if after completing the inventive reaction, 1 L of filtrate solution containing approximately 5% $Na_3TMT$ is obtained having a pH of 14, the amount of TMT in the solution can be adjusted so that the percentage of $Na_3TMT$ in the solution is about 15%. This can be accomplished by the addition of solid TMT 55 (a solid containing about 55% $Na_3TMT$).

Sufficient acid may be added to the solution to reach a pH more characteristic of TMT 15 (pH=12.5), where said acid may be selected from any variety of acids allowing the pH to be adjusted downward to about 12.5. Acids such as bicarbonate, phosphoric or boric acids are recommended because of additional benefit that they impart to the mercapto-s-triazine solution as disclosed in U.S. Pat. No. 5,476,973. The resulting TMT solution will contain about 33% recycled $Na_3TMT$, and will be suitable for the recovery of metals via precipitation.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, are hereby incorporated by reference.

EXAMPLES

Example 1

A 50-ml three-neck round-bottom flask was charged with a Teflon-coated magnetic stir bar and 1 g of Ag-TMT precipitate (52% Silver). The Ag-TMT precipitate was suspended as a slurry in about 20 ml of 1M NaOH. Over the course of about 72 hours, about 0.5 grams of anhydrous $NaBH_4$ was added directly to the Ag-TMT slurry. The concentration of $NaBH_4$ was initially 0.13M, but the reaction was sluggish and the concentration of the solution was increased to about 0.66M. In addition to the increase in reductant concentration, the temperature of the solution was increased to about 50° C. Prior to the increase in the solution concentration and temperature, the reaction progressed slowly. After increasing the reductant concentration and temperature, the reaction proceeded rapidly.

Shiny solid spheres were observed in the bottom of the flask after about 72 hours. The solution no longer had the appearance of a slurry. The solution above the solid was clear and slightly yellow. The solid was separated from the solution by filtration, dried in vacuum and weighed to give 0.52 g, nearly quantitative yield, of Ag metal (96% Ag). The filtrate was neutralized with 2 ml of 10% phosphoric acid. The addition of acid was followed by the formation of hydrogen gas due to the excess $NaBH_4$, and the final pH of the solution was approximately 12. The filtrate was analyzed by ion chromatography to give 0.36g of $Na_3TMT$ in 22 mls of filtrate for a yield of 75%.

This example clearly shows that reaction temperatures above 45° C. and reductant concentrations above about 0.4M accelerate the rate of the inventive reaction. In addition, the example shows that by adding a reducing agent to a slurry of Ag-TMT precipitate, one can isolate nearly pure silver metal and generate a solution containing the TMT precipitating agent. The pH of the reaction mixture was about 14 during the course of the reaction and the reduction potential of the reductant was −1.24 V vs NHE.

Example 2

A 4-ml microflask with gas outlet and addition port was charged with a Teflon coated magnetic stir bar and 0.5 g of Ag-TMT precipitate (52% Silver). $NaBH_4$ (105 mg, 9 times excess) was dissolved into 3 ml of 1M NaOH and added directly to the Ag-TMT precipitate. The mixture of $NaBH_4$ and Ag-TMT precipitate gave a light yellow colored slurry. The concentration of $NaBH_4$ was 0.93M. Then solution was stirred at 40° C. The pH of the reaction mixture was about 14 during the course of the reaction and the reduction potential of the reductant was 1.24 V vs NHE. After about four hours, the slurry was visibly darker but rapid settling of the dark solid in the reaction vessel did not occur when stirring was stopped. (An indication of completion of the reaction between the reductant and the precipitate is the rapid settling of the dark solid product.)

After approximately 24 hrs, the slurry had turned dark brown but still appeared to be a finely divided solid suspended in the solution. Even though the concentration of the reducing agent was increased to about 0.93M the rate of the reaction had increased only moderately compared to example 1. The temperature was increased, and after about 24 hrs at a temperature of about 53 C the stirring was stopped and a shiny glitter-like solid rapidly settled to the bottom of the flask. The solution was clear and slightly yellow. The solid was separated from the solution by filtration, dried in vacuum and weighed to give 0.245 g, 94% yield, of Ag metal (96% Ag). The filtrate was neutralized with 0.5 ml of 10% phosphoric acid. A few drops of 50% NaOH were added to the solution to give a final solution pH of about 12. The solution was analyzed by ion chromatography to give 0.12 g of $Na_3TMT$ in 3 ml's of filtrate for a yield of about 50%.

This example shows that an increase in the concentration of the reducing agent gives a moderate increase in the rate of the reaction. However, a more influential factor in increasing the rate of the reaction is the increase in the reaction temperature.

Example 3

A 4-ml microflask with gas outlet and addition port was charged with a Teflon coated magnetic stir bar and 0.5 g of Ag-TMT precipitate (52% Silver). $NaBH_4$ (76 mg, 5 times excess) was dissolved into 3 ml of 1M NaOH and added directly to the Ag-TMT precipitate. The mixture of $NaBH_4$ and Ag-TMT precipitate gave a light yellow colored slurry. The concentration of NaBH was 0.67M. The reaction temperature was slowly increased during the day in the following progression:

| Elapsed Reaction Time hr's | Temperature (°C.) | Slurry Appearance |
|---|---|---|
| 0 | 25 | yellow slurry |
| 0.3 | 37 | yellow brown slurry |
| 1.3 | 42 | light brown slurry |
| 3 | 55 | darker brown, some foam |

-continued

| Elapsed Reaction Time hr's | Temperature (°C.) | Slurry Appearance |
| --- | --- | --- |
| 5.5 | 58 | dark brown black slurry |
| 7.75 | 65 | dark brown black slurry |
| 8.75 | 65 | dark brown black slurry |
| 23 | 65 | rapid settling shiny solid |

After 23 hrs the stirring was stopped and a shiny glitter-like solid rapidly settled to the bottom of the flask. The solution was clear and slightly yellow-green. 20 The solid was separated from the solution by filtration, dried in vacuum and weighed to give 0.241 g. 93% yield, of Ag metal (96% Ag). The filtrate pH was about 11.5 so that no neutralization was necessary and no unreacted $NaBH_4$ remained in the solution. The solution was analyzed by ion chromatography to give 0. 13g of $Na_3TMT$ in 3 mls of filtrate for a yield of about 50%.

Key features of this example are the decrease in reaction time, which is achieved as a result of increasing the reaction temperature to 65° C., and the decrease in the excess of $NaBH_4$. The pH of the reaction mixture decreased over the time of the reaction with the fmal reducing power of the reductant at about −1.1 V vs NHE.

Example 4

The following were added to a 4 ml reaction vial: 0.5 g Ag-TMr precipitate (42% Ag), 0.24 g $Na_2S_2O_4$ (50% excess, 0.67 M), and 2 ml of a 1.6M NaOH solution. The vial was placed in an oil bath at 70° C. and magnetic stirring was implemented. Immediately, the solution turned a dark green slurry. Within one minute, black solids separated from the solution. The solution was green and transparent. After 2.5 hours, black and gray solids had settled to the bottom of the vial leaving a clear, dark green liquid above. The solution was filtered through a 0.22 cm filter. The solids were dried in a vacuum oven at 40° C. overnight. The solids mass was 0.173 g, of which 99% was Ag metal (81% yield). The filtrate was a light orange color, with a pH=12. About 8.5 ml of a 2.20 g/l $Na_3TMT$ solution was recovered (yield= 6.45%).

This example shows that at a high temperature of about 70° C., the reaction proceeds rapidly with only a 50% excess in reducing agent at a concentration of about 0.67M. While the high reaction temperature increases the rate of the reaction, the yield of TMT is low due to unwanted side reactions. The pH changes over the course of the reaction, but even at the end of the reaction the reductant power is still about −1.0 V vs. NHE.

Example 5

The following were added to a 4 ml reaction vial: 0.253g Ag-TMr precipitate (42% Ag), 0.120 g $Na_2S_2O_4$ (40% excess 0.35 M), and 2 ml of a 1.75 M NaOH solution. The vial was placed in an oil bath at 25° C. and magnetic stirring was implemented. Immediately, the solution turned a dark green slurry. Within 15 minutes, black solids separated from the solution. The solution was green and transparent. After 24 hours, the solution was no longer transparent, but some of the black solids remained. The solution was centrifuged, solids were rinsed and centrifuged again. The liquid was filtered through a 0.22 μm filter, and the solids were dried in a vacuum oven at 40° C. overnight. The solids mass was 0.103 g, of which 92% was Ag metal (89% yield). The filtrate was a pale yellow color, with a pH=14. About 9.7 ml of a 5.26 g/l $Na_3TMT$ solution was recovered (yield= 34.8%).

This example shows that the inventive reaction occurs even at temperatures as low as 25° C. and with reductant excess of only 40%. The pH of the reaction mixture was at least 14 so that the reductant power was always about −1.12 V vs NHE.

Example 6

The following were added to a 4 ml reaction vial: 0.25 g Ag-TMr precipitate (42% Ag), 0.078 g $Na_2SO_3$ (25% excess 0.41 M), and 1.5ml of a 1.75M NaOH solution. The vial was placed in an oil bath at 70° C. and magnetic stirring was implemented. After 41 hours, the solution was a gray colloidal suspension and the reaction appeared to be finished. At that time, the reaction was stopped and the solution was filtered through a 0.22 gm filter. The filtered solid was a black paste. The paste was dried in a vacuum oven at 40° C. overnight. The solids mass was 0. 135 g, of which 70% was Ag metal (90% yield). The filtrate was a pale yellow color with a pH=14. About 4.7 ml of a 2.51 g/l $Na_3TMT$ solution was recovered (yield=8.14%).

This example shows that lower reducing power reductants (−0.9 V vs NHE) are less efficient in the method of this invention, but that a significant amount of the Ag-TMT precipitate starting material was converted to silver metal with only a small yield of TMT due to side reactions at the high temperature of 70 C. The transformation occurred with only a slight excess in reducing agent of 25%.

Example 7

To show that TMT had been obtained as a result of the inventive reaction, the resultant filtrate from several of the examples was added to bleach fix or fix solutions containing dissolved silver. In every case, a yellow precipitate was formed immediately on contact with the silver-bearing solution, indicating the formation of Ag-TMT solid.

This example verifies that the precipitating agent TMT still functions as expected after resolubilization by the method of this invention.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for recovering silver-metal and mercapto-s-triazine from precipitates recovered from photographic solutions which comprises adding a reducing agent to a slurry of silver-mercapto-s-triazine precipitate having a pH above about 5 and reducing the silver-mercapto-s-triazine to silver metal and soluble mercapto-s-triazine or a salt thereof.

2. A process as in claim 1, wherein the temperature of the slurry is maintained in the range of 15° C. to 100° C. during the reduction of silver-mercapto-s-triazine to silver metal and soluble mercapto-s-triazine or salt thereof.

3. A process as in claim 2, wherein the concentration of reducing agent within the slurry is maintained above 0.05 molar.

4. A process as in claim 3, wherein the reducing agent has a reducing power more negative than about −0.9 V vs. the Normal Hydrogen Electrode.

5. A process as in claim 4, wherein the reducing agent is employed in an amount of at least one molar equivalent per mole of silver within said slurry.

6. A process as in claim 1, wherein the temperature of the slurry is maintained in the range of 45° C.–65° during the reduction of silver-mercapto-s-triazine to silver metal and soluble mercapto-s-triazine.

7. A process as in claim 1, wherein the pH of said slurry is above about 11.

8. A process as in claim 1, wherein the pH of said slurry is above about 14.

9. A process as in claim 1, wherein the concentration of reducing agent within said slurry is maintained above 0.4M.

10. A process as in claim 8, wherein the reducing agent has a pH dependent reducing potential.

11. A process as in claim 1, wherein the reducing agent is selected from $NaBH_4$, $Na_2S_2O_4$ and $Na_2SO_3$.

12. A process as in claim 1, wherein the mercapto-s-triazine is selected from the group consisting of trimercapto-s-triazine and the trisodium salt thereof.

13. A process for recovering trimercapto-s-triazine and salts thereof from silver-mercapto-s-triazine precipitates recovered from photographic solutions which comprises adding a reducing agent having a reducing power more negative than about −0.9 V vs. the Normal Hydrogen Electrode to an aqueous slurry of silver-trimercapto-s-triazine precipitate having a pH above about 11 and reducing the silver-trimercapto-s-triazine to silver and soluble trimercapto-s-triazine or a salt thereof.

14. A process as in claim 13, wherein the concentration of reducing agent within said slurry is above 0.4M and the temperature of said slurry is maintained in the range of 30° C.–75° C. during the reduction of silver-trimercapto-s-triazine to silver metal and soluble trimercapto-s-triazine or salt thereof.

15. A process as in claim 14, wherein the reducing agent is employed in an amount of at least one molar equivalent per mole of silver within said aqueous slurry.

16. A process as in claim 15, wherein the reducing agents are selected from $NaBH_4$, $Na_2S_2O_4$ and $Na_2SO_3$.

17. A process for refining silver which comprises a process of claim 1.

18. A process as in claim 1 comprising the additional steps of separating the silver metal from the solution containing soluble mercapto-s-triazine or salt thereof and adjusting the concentration of soluble mercapto-s-triazine or salt thereof within said solution to a value above 5 wt. % and adjusting the pH of the solution of soluble mercapto-s-triazine or salt thereof to a value of about 12.5.

19. A process as in claim 1, wherein over 50% of the mercapto-s-triazine in the silver-mercapto-s-triazine precipitate is recovered as soluble mercapto-s-triazine.

* * * * *